United States Patent [19]

Zeugner et al.

[11] 4,325,957
[45] Apr. 20, 1982

[54] 2-ACYLAMINOMETHYL-1,4-BENZODIAZE-PINE DERIVATIVES AND THEIR SALTS AND PHARMACEUTICAL COMPOSITIONS THEREOF

[75] Inventors: Horst Zeugner, Hanover, Fed. Rep. of Germany; Dietmar Roemer, Allschwil, Switzerland; Hans Liepmann, Hanover; Wolfgang Milkowski, Burgdorf, both of Fed. Rep. of Germany

[73] Assignee: Kali-Chemie Pharma GmbH., Hanover, Fed. Rep. of Germany

[21] Appl. No.: 219,487

[22] Filed: Dec. 23, 1980

[30] Foreign Application Priority Data

Dec. 24, 1979 [DE] Fed. Rep. of Germany ....... 2952279

[51] Int. Cl.³ ................ C07D 401/12; C07D 403/12; C07D 405/12; C07D 409/12
[52] U.S. Cl. ............................. 424/263; 260/239 BD; 260/244.4; 260/245.7; 260/330.3; 260/347.3; 424/274; 424/275; 424/285
[58] Field of Search ............... 260/244.4, 245.7, 330.3, 260/347.3; 424/263, 274, 275, 285

[56] References Cited

U.S. PATENT DOCUMENTS 3,738,999 6/1973 Krapcho et al. ............ 260/347.3 X
3,947,475 3/1976 DeBaun et al. ................. 260/347.3

FOREIGN PATENT DOCUMENTS 2353160 11/1974 Fed. Rep. of Germany .
2436147 2/1975 Fed. Rep. of Germany .

*Primary Examiner*—Richard Raymond
*Attorney, Agent, or Firm*—Schwartz, Jeffery, Schwaab, Mack, Blumenthal & Koch

[57] ABSTRACT

Novel 2-acylaminomethyl-1H-2,3-dihydro-1,4-benzodiazepine derivatives are disclosed which possess the Formula I

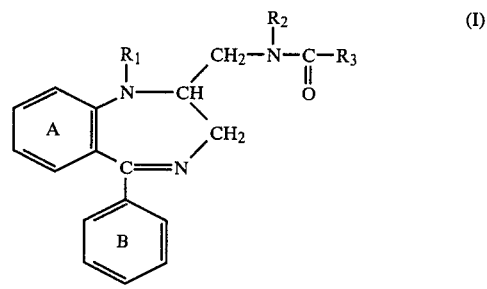

wherein
$R_1$ represents hydrogen, lower akyl, lower alkenyl or cyclopropylmethyl;
$R_2$ represents hydrogen, lower alkyl or lower alkenyl;
$R_3$ represents a group of the formula a, b, c or d;

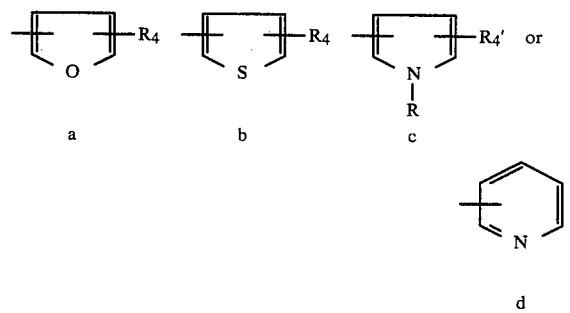

wherein
R is hydrogen or $C_1-C_3-$ alkyl;
$R_4$ is hydrogen, lower alkyl, lower alkoxy, nitro or halogen, and
$R_4'$ is hydrogen or $C_1-C_4-$ alkyl and the aromatic groups A and B may be unsubstituted or substituted by 1 to 3 substituents such as halogen, lower alkylthio, lower alkoxy, lower alkyl, hydroxy, nitro, trifluoromethyl or methylenedioxy or ethylenedioxy and optical isomers and acid addition salts of the compounds. In addition to psycho pharmacological, diuretic and antiarrhythmic properties, the novel compounds of Formula I possess primarily outstanding analgesic activities and are low in toxicity. The compounds are prepared by acylating 2-aminomethyl-1,4-benzodiazepine derivatives with corresponding carbonic acid derivatives. Furthermore, 2-azidomethyl-1,4-benzodiazepine derivatives are disclosed which provide valuable intermediates for the preparation of the compounds of Formula I yet also possess themselves pharmacological activities.

21 Claims, No Drawings

2-ACYLAMINOMETHYL-1,4-BENZODIAZEPINE DERIVATIVES AND THEIR SALTS AND PHARMACEUTICAL COMPOSITIONS THEREOF

BACKGROUND OF THE INVENTION

The present invention relates to novel 2-acylaminomethyl-1,4-benzodiazepine derivatives, their salts and processes for their preparation and pharmaceutical compositions thereof and methods of treatment using same.

The German Offenlegungsschrift No. 2 353 187 discloses inter alia 2-acylaminomethyl-1,4-benzodiazepine derivatives wherein the acyl group is a lower alkanoyl. These compounds possess a primarily anti-convulsive activity.

SUMMARY OF THE INVENTION

It is an object of the present invention to provide novel 2-acylaminomethyl-1,4-benzodiazepine derivatives and pharmaceutical compositions thereof which possess a novel pharmacological activity profile.

In particular it is an object of the present invention to provide 2-acylaminomethyl-1,4-benzodiazepine derivatives which possess strong analgesic activities in addition to psycho pharmacological, diuretic and antiarrhythmic properties. It is a further object of the present invention to provide such compounds and pharmaceutical compositions thereof which are low in toxicity and exhibit a high therapeutic index.

It is a further object of the present invention to provide processes for preparing such novel 2-acylaminomethyl-1,4-benzodiazepine derivatives with improved pharmacological properties.

It is a further object of the present invention to provide novel 2-azidoaminomethyl-1,4-benzodiazepine derivatives which are useful intermediates in the preparation of the novel 2-acylaminomethyl-1,4-benzodiazepine derivatives of the present invention and which themselves possess valuable pharmacological properties.

In order to accomplish the foregoing objects according to the present invention, there are provided novel 2-acylaminomethyl-1H-2,3-dihydro-1,4-benzodiazepine derivatives of the Formula I

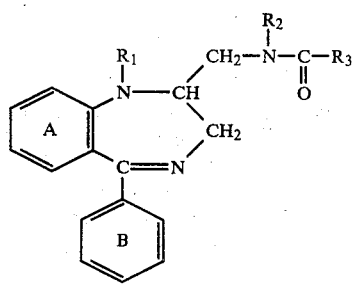

wherein
$R_1$ represents hydrogen, lower alkyl, lower alkenyl or cyclopropylmethyl,
$R_2$ represents hydrogen, lower alkyl or lower alkenyl,
$R_3$ represents a group of the formula a, b, c, or d

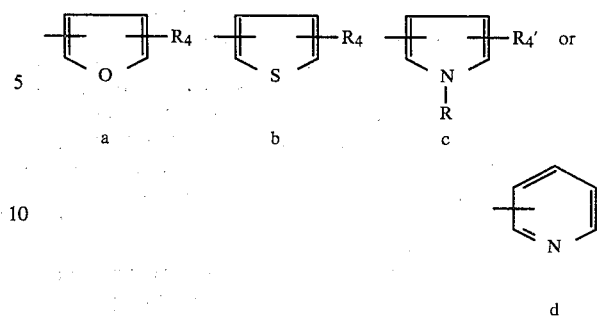

wherein R is hydrogen or $C_1-C_3$-alkyl, $R_4$ is hydrogen lower alkyl, lower alkoxy, nitro or halogen, in particular chlorine or bromine, and $R_4'$ is hydrogen or $C_1-C_4$-alkyl, and the aromatic groups A and B independently from each other each may be unsubstituted or be substituted by 1 to 3 substituents selected from the group consisting of halogen, lower alkythio, lower alkoxy, lower alkyl, hydroxy, nitro and trifluoromethyl, or be substituted at two adjacent carbon atoms by methylenedioxy or ethylenedioxy, and optical isomers and pharmaceutically-acceptable acid addition salts thereof.

The compounds exhibit valuable pharmacological properties. In particular in addition to psycho pharmacological, diuretic and antiarrhythmic properties, these compounds primarily exhibit strong analgesic activities due to which they are useful in the treatment of pains.

According to the present invention, there are further provided pharmaceutical compositions comprising an analgesically effective amount of the above-defined compounds and a pharmaceutically acceptable diluent.

According to the present invention, there are further provided processes for preparing the compounds of Formula I in good yields.

According to the present invention, compounds of Formula I can be prepared by acylating an amino compound of Formula II

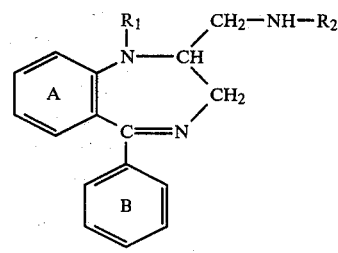

wherein A, B, $R_1$ and $R_2$ are as defined above or an acid addition salt thereof with a reactive carbonic acid derivative of Formula III

wherein $R_3$ is as defined above and Y represents hydroxy, halogen, lower alkoxy, or a group O—CO—Z wherein Z represents $R_3$ or lower alkoxy.

Subsequently, compounds of Formula I wherein $R_2$ represents hydrogen may be alkylated into compounds of Formula I wherein $R_2$ represents lower alkyl. Also chloro, bromo or nitro substituents may be introduced into the phenyl ring A of compounds of Formula I subsequent to the above acylating reaction.

The compounds of Formula I may be recovered from the respective reaction solutions in the form of optical isomers or of racemic mixtures in form of the free bases or in form of the acid addition salts. Acid addition salts may be transformed into free bases and vice versa according to conventional methods. Racemic mixtures may be separated into the optical isomers according to conventional methods.

According to the present invention there are further provided novel 2-azidomethyl-1,4-benzodiazepine derivatives of Formula X

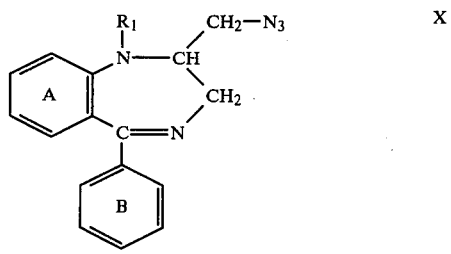

wherein A, B and $R_1$ are as defined above.

The compounds of Formula X are novel and represent valuable intermediates for the preparation of compounds of Formula I. Additionally, the compounds of Formula X themselves exhibit valuable pharmacological properties, in particular, bronchal-dilating, sedative and antiarrhythmic properties, due to which they are useful as sedatives, broncholytic and antiarrhythmic agents.

Further objects, features and advantages of the present invention will become apparent from the detailed description of the invention which follows.

DETAILED DESCRIPTION OF THE INVENTION AND ITS PREFERRED EMBODIMENTS

It has been found that the above-defined compounds of Formula I possess the above-mentioned pharmacological activities and at the same time are low in toxicity and thus exhibit a high therapeutic index.

If in the compounds of Formula I, $R_1$ or $R_2$ represent lower alkyl or alkenyl, these groups may contain up to four carbon atoms and may be straight or branched. Suitable such groups are methyl, ethyl, propyl, isopropyl, n-butyl, 1-methylpropyl, 2-methylpropyl, tert.-butyl, allyl, 2-butenyl or 3-butenyl.

If $R_4$ represents lower alkyl, this group may contain 1 to 4 carbon atoms and may represent one of the above-mentioned lower alkyl groups. Lower alkoxy may contain 1 to 4 carbon atoms and may be straight or branched.

The alkyl group within alkyl, alkylthio or alkoxy substituents of the phenyl groups A and/or B also may contain 1 to 4 carbon atoms and may be one of the above-mentioned groups. Methyl and ethyl substituents are preferred in particular in the case of di- and tri-substitution of the phenyl ring. Suitable halogen substituents include fluorine, chlorine and bromine. In the case of substitution of the phenyl ring with alkylthio, nitro or trifluoromethyl, mono-substitution is preferred. In the case of substitution with halogen and/or alkyl and/or alkoxy or hydroxy, mono- and disubstitution are preferred. In the case of lower alkoxy substituents, in particular methoxy, tri-substitution is also favorable.

It is known in the art (see for example German Offenlegungsschrift No. 2 520 937 and No. 2 754 112) that 1,4-benzodiazepine derivatives which are substituted in the 2-position possess valuable pharmacological properties and are low in toxicity. In particular, the known compounds influence specifically the central nervous system. The effect of these known compounds are such that due to their anxiolytic and anti-aggressive properties, they present useful therapeutic agents for the treatment of these symptoms in humans.

It is surprising that the novel 2-acylaminomethyl-1,4-benzodiazepine derivatives of the present invention possess a novel and different pharmacological activity profile in that they possess outstanding analgesic activities in addition to psycho pharmacological, diuretic and antiarrhythmic properties and are low in toxicity. The compounds of Formula I exhibit analgesic activities in various standard tests in small rodents and in monkeys.

The compounds of Formula I according to the present invention are useful as analgesics in the treatment of pain due to their outstanding analgesic activities which can be demonstrated by their capability to increase the pain threshold in mammals.

This analgesic activity has been evaluated in two pharmacological standard methods, the tail flick test in mice and the arthritis pain test in rats.

DESCRIPTION OF THE PHARMACOLOGICAL TEST METHODS

1. Determination of the Minimal Toxic Dose

Maximum doses of 300 mg/kg of the test compound are administered orally to three male mice having a weight of 20–25 g and toxicity symptoms are carefully observed for a period of three hours. Furthermore, over a period of 24 hours from the administration all symptoms and deaths are registered. Side-symptoms are also observed and registered. Depending on their water solubility, the test compounds are administered either in form of aqueous solutions or in form of suspensions without the use of solvents. In order to maintain a stable suspension of the test compound, one drop of Tween-80 can be added and the mixture can be mechanically homogenized. In the case of compounds where deaths or toxic symptoms have been observed, additional mice are treated with decreasing doses until a dose is reached at which no toxic symptoms occur. The lowest dose which causes toxic symptoms is considered the minimal toxic dose.

2. Arthritis Pain Test in Rats

Male rats having a weight of from 160 to 180 g are anesthetized by small i.p. injection of 20 mg/kg of sodium pentobarbital and 0.1 ml of a suspension of mycobacterium smegmae (SI 043) in liquid paraffin (0.6 mg mycobacterium/0.1 ml of oil) are injected intracutaneously into the left rear paw. Fourteen days later when a marked secondary arthritis has developed in particular in the right rear paw, the effect of the test compound is evaluated. A control-reading is taken 30 minutes prior to administration of the test compound by bending the foot joint of the right rear paw three times and counting the number of squeakings. Rats which do not react are eliminated from the test. Three hours after oral administration of the test compound the bending of the joint is repeated. Animals which squeak only once or not at all are considered to be protected against pain. Between about 9 and 20 rats are used per dose and the $ED_{50}$ (95% reliability) is determined according to the method of Litchfield and Wilcoxon (1949). The dose which provides protection in 50% of the treated animals is taken as $ED_{50}$.

3. Tail Flick Test in Mice

This test is carried out according to the method described by D'Amour and Smith (1941), yet fed male and female mice having a body weight of 16 to 25 g are used instead of rats. Thirty minutes prior to treatment with the test compound, each mouse is placed separately in a cylindrical container in such a manner that it cannot turn itself or move forward. Its tail is positioned in a narrow groove projecting out of the container. A certain point of the tail of each animal (about 35 mm beyond the root of the tail) is subjected to the heat beam of a lamp of known strength and temperature which is positioned directly under the tail. The number of seconds which pass before the mouse moves its tail out of the light beam is determined twice, once 30 minutes and once 15 minutes prior to subcutaneous administration of the test compound (10 mg/kg). Mice which show a reaction time differing more than 25% are eliminated from the test. The reaction time is again determined 15 minutes and 30 minutes after the treatment and an increase of the reaction period of more than 75% of the average values prior to treatment in the same animal is considered as showing an analgesic effect. The $ED_{50}$ (95% reliability) of each test compound 30 minutes after administration is evaluated according to the method of Litchfield and Wilcoxon (1949). The dose which increases the reaction time as compared to the reaction time prior to treatment for more than 75% in 50% of the animals is considered as $ED_{50}$.

The following compounds were tested according to the foregoing tests:

1. 1-methyl-2-[(thiophene-2-carbonyl)-aminomethyl]-5-phenyl-1H-2,3-dihydro-1,4-benzodiazepine (Sesquitartrate/hemiisopropylate)
2. 1-methyl-2-[(furane-2-carbonyl)-aminomethyl]-5-phenyl-1H-2,3-dihydro-1,4-benzodiazepine (hydrochloride/semihydrate)
3. 8-methoxy-1-methyl-2-[(thiophene-2-carbonyl)-aminomethyl]-5-phenyl-1H-2,3-dihydro-1,4-benzodiazepine (hydrochloride)
4. 8-methoxy-1-methyl-2-[(furane-2-carbonyl)-aminomethyl]-5-phenyl-1H-2,3-dihydro-1,4-benzodiazepine (hydrochloride)
5. 8-methoxy-1-methyl-2-[(thiophene-3-carbonyl)-aminomethyl]-5-phenyl-1H-2,3-dihydro-1,4-benzodiazepine (hydrochloride)
6. 8-methoxy-1-methyl-2-[(furane-3-carbonyl)-aminomethyl]-5-phenyl-1H-2,3-dihydro-1,4-benzodiazepine (hydrochloride)
7. 1-methyl-2-[(thiophene-3-carbonyl)-aminomethyl]-5-phenyl-1H-2,3-dihydro-1,4-benzodiazepine (hydrochloride)
8. 1,7,8-trimethyl-2-[(furane-3-carbonyl)-aminomethyl]-5-phenyl-1H-2,3-dihydro-1,4-benzodiazepine (hydrochloride)
9. 8-methoxy-1-methyl-2-[(5-methylthiophene-2-carbonyl)-aminomethyl]-5-phenyl-1H-2,3-dihydro-1,4-benzodiazepine (hydrochloride)
10. 1,7-dimethyl-2-[(thiophene-3-carbonyl)-aminomethyl]-5-phenyl-1H-2,3-dihydro-1,4-benzodiazepine (dihydrochloride)
11. 1,7-dimethyl-2-[(furane-3-carbonyl)-aminomethyl]-5-phenyl-1H-2,3-dihydro-1,4-benzodiazepine (hydrochloride)
12. 1-methyl-2-[(5-methylthiophene-2-carbonyl)-aminomethyl]-5-phenyl-1H-2,3-dihydro-1,4-benzodiazepine (hydrochloride; 0.4 acetone)
13. 8-ethoxy-1-methyl-2-[(furane-3-carbonyl)-aminomethyl]-5-phenyl-1H-2,3-dihydro-1,4-benzodiazepine (hydrochloride; 0.5 water; 0.5 acetone)
14. 1-methyl-2-[(furane-2-carbonyl)-aminomethyl]-5-(3-methoxyphenyl)-1H-2,3-dihydro-1,4-benzodiazepine (hydrochloride)
15. 7-methoxy-1-methyl-2-[(furane-3-carbonyl)-aminomethyl]-5-phenyl-1H-2,3-dihydro-1,4-benzodiazepine (sequihydrochloride; 0.3 water)
16. 1-methyl-2-[(thiophene-3-carbonyl)-aminomethyl]-5-(3-methoxyphenyl)-1H-2,3-dihydro-1,4-benzodiazepine (hydrochloride)
17. 1-ethyl-2-[(furane-3-carbonyl)-aminomethyl]-5-phenyl-1H-2,3-dihydro-1,4-benzodiazepine (hydrochloride; 0.15 water)
18. 1-methyl-2-[(furane-2-carbonyl)-aminomethyl]-5-(2-fluorophenyl)-1H-2,3-dihydro-1,4-benzodiazepine (hydrochloride)
19. 1-methyl-2-[(furane-3-carbonyl)-aminomethyl]-5-(2-fluorophenyl)-1H-2,3-dihydro-1,4-benzodiazepine (hydrochloride)
20. 1-methyl-2-[(thiophene-3-carbonyl)-aminomethyl]-5-(2-fluorophenyl)-1H-2,3-dihydro-1,4-benzodiazepine (hydrochloride)
21. 1-methyl-2-[(thiophene-2-carbonyl)-aminomethyl]-5-(2-fluorophenyl)-1H-2,3-dihydro-1,4-benzodiazepine (hydrochloride)
22. 1-methyl-2-[(furane-3-carbonyl)-aminomethyl]-5-phenyl-2,3-dihydro-1,4-benzodiazepine
23. 8-methoxy-1-methyl-2-[(3-methylthiophene-2-carbonyl)-aminomethyl]-5-phenyl-1H-2,3-dihydro-1,4-benzodiazepine (hydrochloride)
24. 7,8-methylenedioxy-1-methyl-2-[(thiophene-2-carbonyl)-aminomethyl]-5-phenyl-1H-2,3-dihydro-1,4-benzodiazepine (hydrochloride)
25. 7,8-methylenedioxy-1-methyl-2-[furane-2-carbonyl)-aminomethyl]-5-phenyl-1H-2,3-dihydro-1,4-benzodiazepine (hydrochloride)
26. 7,8-methylenedioxy-1-methyl-2-[(furane-3-carbonyl)-aminomethyl]-5-phenyl-1H-2,3-dihydro-1,4-benzodiazepine
27. 8-methoxy-1-methyl-2-[(5-bromothiophene-2-carbonyl)-aminomethyl]-5-phenyl-1H-2,3-dihydro-1,4-benzodiazepine (hydrochloride)
28. 2-[(thiophene-2-carbonyl)-aminomethyl]-5-phenyl-1H-2,3-dihydro-1,4-benzodiazepine
29. 8-methoxy-1-methyl-2-nicotinoylaminomethyl-5-phenyl-1H-2,3-dihydro-1,4-benzodiazepine (dihydrochloride; 0.4 water; 0.8 acetone)
30. 8-methoxy-1-methyl-2-picolinoylaminomethyl-5-phenyl-1H-2,3-dihydro-1,4-benzodiazepine (1.8 hydrochloride)
31. 8-methoxy-1-methyl-2-[(5-methylfurane-2-carbonyl)-aminomethyl]-5-phenyl-1H-2,3-dihydro-1,4-benzodiazepine (hydrochloride)
32. 7,8-methylenedioxy-1-methyl-2-[(5-methylthiophene-2-carbonyl)-aminomethyl]-5-phenyl-1H-2,3-dihydro-1,4-benzodiazepine
33. 8-methoxy-1-methl-2-[(1-methylpyrrol-2-carbonyl)-aminomethyl]-5-phenyl-1H-2.3-dihydro-1,4-benzodiazepine (hydrochloride)

34. 8-methoxy-1-methyl-2-[(furane-3-carbonyl)-aminomethyl]-5-(4-fluorophenyl)-1H-2,3-dihydro-1,4-benzodiazepine (hydrochloride)
35. 8-methoxy-1-methyl-2-[(furane-3-carbonyl)-aminomethyl]-5-(2-trifluoromethylphenyl)-1H-2,3-dihydro-1,4-benzodiazepine (hydrochloride)
36. 1-methyl-2-[(1-methylpyrrol-2-carbonyl)-aminomethyl]-5-phenyl-1H-2,3-dihydro-1,4-benzodiazepine (hydrochloride)
37. 8-chloro-1-methyl-2-[(furane-3-carbonyl)-aminomethyl]-5-phenyl-1H-2,3-dihydro-1,4-benzodiazepine (hydrochloride)
38. 8-fluoro-1-methyl-2-[(furane-3-carbonyl)-aminomethyl]-5-phenyl-1H-2,3-dihydro-1,4-benzodiazepine (hydrochloride)
39. 8-methoxy-1-methyl-2-[(furane-3-carbonyl)-aminomethyl]-5-(2-fluorophenyl)-1H-2,3-dihydro-1,4-benzodiazepine (hydrochloride)
40. 8-methoxy-1-methyl-2-[(thiophene-2-carbonyl)-aminomethyl]-5-(2-fluorophenyl)-1H-2,3-dihydro-1,4-benzodiazepine (hydrochloride)
41. 7,8-methylenedioxy-1-methyl-2-[(thiophene-3-carbonyl)-aminomethyl]-5-phenyl-1H-2,3-dihydro-1,4-benzodiazepine (hydrochloride)
42. 8-methoxy-1-methyl-2-[(furane-3-carbonyl)-aminomethyl]-5-(3-fluorophenyl)-1H-2,3-dihydro-1,4-benzodiazepine (hydrochloride)
43. 8-fluoro-1-methyl-2-[(5-methylthiophene-2-carbonyl)-aminomethyl]-5-phenyl-1H-2,3-dihydro-1,4-benzodiazepine (hydrochloride)
44. 7,8-ethylenedioxy-1-methyl-2-[(furane-3-carbonyl)-aminomethyl]-5-phenyl-1H-2,3-dihydro-1,4-benzodiazepine (hydrochloride)
45. 1,7-dimethyl-2-[(furane-3-carbonyl)-aminomethyl]-5-(2-fluorophenyl)-1H-2,3-dihydro-1,4-benzodiazepine (1.4 hydrochloride; 0.5 water; 0.2 ethylacetate)
46. 8-methoxy-1-methyl-2-[(5-bromothiophene-2-carbonyl)-aminomethyl]-5-(2-fluorophenyl)-1H-2,3-dihydro-1,4-benzodiazepine (hydrochloride)
47. 8-methoxy-1-methyl-2-[(thiophene-2-carbonyl)-aminomethyl]-4-(4-fluorophenyl)-1H-2,3-dihydro-1,4-benzodiazepine (hydrochloride)
48. 8-methoxy-1-methyl-2-[(5-bromothiophene-2-carbonyl)-aminomethyl]-5-(3-fluorophenyl)-1H-2,3-dihydro-1,4-benzodiazepine (hydrochloride)
49. 8-methoxy-1-methyl-2-[(5-bromothiophene-2-carbonyl)-aminomethyl]-5-(4-fluorophenyl)-1H-2,3-dihydro-1,4-benzodiazepine (hydrochloride)

The results of the pharmacological tests are given in the table below.

The results show that the compounds of the present invention considerably increase the pain threshhold in mammals and humans. Accordingly, the compounds of the present invention are valuable analgesics for the treatment of all types of pain. The administered doses can vary depending on the type of the compound, the mode of administration and the treated condition. Suitable doses for larger mammals may vary in the range of between about 0.1 and about 100 mg/kg.

| Compound NO. | MDL (mouse) p.o. mg/kg | Tail Flick Test (mouse) s.c. ED$_{50}$ mg/kg | Arthritis Pain Test (Rat) p.o. ED$_{50}$ mg/kg |
| --- | --- | --- | --- |
| 1 | >300 | 2.8 | 13 |
| 2 | >300 | 2.8 | 32 |
| 3 | >200 | 5.3 | 20 |
| 4 | >200 | 7.0 | 21 |
| 5 | >200 | 2.4 | 15 |
| 6 | >50 | 2.8 | 9 |
| 7 | >200 | 0.22 | 19 |
| 8 | >200 | 8.0 | 14 |
| 9 | >200 | 5.6 | 14 |
| 10 | >300 | 3.2 | 32 |
| 11 | >300 | 1.2 | 30 |
| 12 | >300 | 2.8 | 10 |
| 13 | >200 | 6.0 | 15 |
| 14 | >300 | 1.6 | 32 |
| 15 | >300 | 8.5 | 32 |
| 16 | >300 | 0.5 | 32 |
| 17 | >200 | 2.6 | 22 |
| 18 | >300 | 4.1 | 18 |
| 19 | >300 | 0.56 | 13 |
| 20 | >300 | 1.1 | 18 |
| 21 | >300 | 6.2 | 13 |
| 22 | | 0.44 | 14 |
| 23 | | 7.2 | 25 |
| 24 | | 3.8 | 10 |
| 25 | | <5.6 | <32 |
| 26 | | 2.0 | <5.6 |
| 27 | | >5.6 | <32 |
| 28 | | 4.2 | >32 |
| 29 | | 4.0 | 30 |
| 30 | | 7.0 | >32 |
| 31 | | 4.4 | 30 |
| 32 | | 5.6 | <18 |
| 33 | | 1.0 | <18 |
| 34 | | 2.1 | 5.6 |
| 35 | | 1.0 | <18 |
| 36 | | 2.1 | >18 |
| 37 | | 1.2 | >18 |
| 38 | | 0.32 | <18 |
| 39 | | 0.7 | <10 |
| 40 | | 1.2 | <18 |
| 41 | | 2.1 | 5.6 |
| 42 | | 5.6 | <18 |
| 43 | | 5.6 | <18 |
| 44 | | >5.6 | <18 |
| 45 | | 3.8 | <18 |
| 46 | | 5.6 | <18 |
| 47 | | .32 | <18 |
| 48 | | >5.6 | <18 |
| 49 | | >5.6 | <18 |

For the above-described medical applications the compounds of Formula I can be used in the form of free bases as well as in the form of pharmaceutically acceptable acid addition salts, that is, salts with such acids the anions of which are non-toxic at the dosage in question. Furthermore, it is advantageous to use such salts for the medical applications which are readily crystallizable and are not or only slightly hydroscopic. Examples of acids which are suitable for salt-formation with compounds of Formula I are the following: hydrochloric acid, hydrobromic acid, sulfuric acid, phosphoric acid, methylsulfonic acid, ethylsulfonic acid, benzene sulfonic acid, p-toluene sulfonic acid, citric acid, acetic acid, lactic acid, succinic acid, maleic acid, fumaric acid, malic acid, tartaric acid, benzoic acid, phenylacetic acid and mandelic acid.

According to a feature of the present invention, there are further provided pharmaceutical compositions containing an effective amount of at least one of the compounds of Formula I or their pharmaceutically acceptable salts. The amount of active ingredient per dosage unit form may vary between about 0.1 and about 100 mg whereby the dosage is chosen depending on the type of species to be treated and the requirement for a given individual treatment. Generally, compositions for parental administration would contain lower amounts of active ingredient than compositions for oral application. The compounds of Formula I may be applied alone or in combination with pharmaceutically acceptable carrier materials and/or adjuvants in many different dosage forms. For example, formulations for oral application may be in the form of solid formulations such as tablets, capsules, powders, granulates, coated tablets and the like. Suppositories can also be used. Solid formulations may comprise conventional pharmaceutically acceptable inorganic carrier materials such as talcum or an organic carrier material such as lactose or starch. Conventional pharmaceutical adjuvants such as magnesium stearate (as lubricant) may also be included. Liquid formulations such as solutions, suspensions, or emulsions may comprise conventional pharmaceutical diluents such as water, vaseline, suspending agents such as polyoxyethylene glycols and the like. Furthermore, conventional adjuvants such as preserving agents, stabilizing agents and emulsifiers may be added.

According to the present invention the 2-acylaminomethyl-1H-2,3-dihydro-1,4-benzodiazepine derivatives of Formula I are prepared by acylating an amino compound of Formula II or an acid addition salt thereof with a carbonic acid or a reactive carbonic acid derivative of Formula III. The acylation can be effected in a conventional manner. Suitably, the acylation is carried out in an inert solvent at a temperature of between about −30° C. and the boiling point of the solvent under normal atmospheric pressure or under elevated pressure.

If a carbonic acid halogenate or a carbonic acid anhydride is used as an acylating agent, the reaction suitably is carried out in the presence of an acid-binding agent such as an alkali metal carbonate or alkali metal hydroxide such as potassium carbonate, sodium carbonate or potassium hydroxide or an organic tertiary amine for example triethylamine, tripropylamine, tributylamine, or pyridine. 4-dimethylaminopyridine or 4-pyrrolidinopyridine also are very suitable. An excess of such tertiary amines may additionally serve as an inert solvent.

Examples of suitable inert solvents include methylene chloride, chloroform, acetone, methylisobutylketone, tetrahydrofurane, dioxane, benzene, toluene, xylene, or chlorobenzene.

If carbonic acid esters, that is compounds of Formula III wherein Y represents lower alkoxy, are used as acylating agents, the reaction suitably is carried out in a closed vessel. An excess of the carbonic acid ester may serve as a solvent. The reaction can be catalyzed by addition of a metal alkylate, for example, by addition of aluminum isopropylate.

If a compound of Formula III is used wherein Y is halogen, such compounds of Formula III wherein Y is chlorine are particularly suitable.

The novel compounds of Formula I also can be prepared by reacting a compound of Formula II wherein A, B, $R_1$ and $R_2$ are as defined above with a carbonic acid of the Formula IV

(IV)

wherein $R_3$ is as defined above. This reaction is suitably carried out in an inert solvent at temperatures of from about −30° C. to boiling temperature of the solvent in the presence of a suitable coupling agent such as dicyclohexylcarbodiimide, carbonyldiimidazol or the like. Preferably the reaction is carried out at a temperature of from about −30° to about +30° C. in an inert solvent such as methylene chloride, chloroform, benzene, or toluene.

Resulting compounds of Formula I wherein $R_2$ represents hydrogen can subsequently be converted into the corresponding N-alkyl compounds by alkylation in a conventional manner. For example, such an alkylation can be effected by replacing the hydrogen in a compound of Formula I wherein $R_2$ is hydrogen by a metal by reacting the compound of Formula I with a metallating agent in a suitable inert solvent and subsequently reacting the metallated compound with an alkyl halogenide, alkylsulfate or alkylsulfonic acid ester.

The metallating reaction as well as the alkylation can be carried out at temperatures of from about −80° C. to boiling temperature of the solvent.

Suitable metallating agents are, for example, sodium hydride, lithiumbutyl, lithiumphenyl, sodiumamide, lithiumdiisopropylamide, and also sodiumalkoxide and thallium-I-alkoxide.

Suitable inert solvents can be chosen depending on the metallating agent which is used. Examples of suitable such solvents include diethylether, tetrahydrofurane, dioxane, benzene, toluene, dimethylformamide, dimethylsulfoxide, and in the case of metal alkoxides also the corresponding alcohols, that is methanol in the case of methyl alcoholates and ethanol in the case of ethyl alcoholates.

By means of the foregoing processes, the compounds of Formula I are obtained in racemic form. The present invention includes the compounds of Formula I in the form of racemic mixtures as well as in optically active forms. The optically active compounds can be obtained from racemic mixtures of compounds of Formula I in conventional manner by salt formation with suitable optically active acids and subsequent fractionated crystallization of the optically active antipodes of the resulting salts (see S. W. Willen, A. Collet, J. Jacques, Tetrahedron 33, (1977) 2725–2736). Examples of suitable optically active acids include tartaric acid, O,O'-dibenzoyl tartaric acid, mandelic acid, di-O-isopropylidene-2-oxo-L-gulonic acid. The obtained salts can be transformed into the free bases which, if desired, subsequently can be transformed into pharmacologically acceptable salts. The racemic mixtures, as well as the optically active isomers and the acid addition salts can be purified by recrystallization from solvents such as lower alkyl alcohols and/or ethers.

Yet the separation of racemic mixtures into the optically active compounds may also be performed at a suitable primary reaction step.

The preparation of the 2-aminomethyl-1H-2,3-dihydro-1,4-benzodiazepine derivatives of Formula II which are used as starting materials, can be done in a known manner according to processes which are disclosed in German Offenlegungsschrift No. 2 221 558. 1-acyl-2-hydroxy-1,3-diaminopropane compounds are used as starting materials for compounds of Formula II and can be prepared according to the method disclosed in German Offenlegungsschrift Nos. 2 221 558, 2 314 993, 2 270 915 and 2 720 968.

The 2-hydroxy-1,3-diaminopropane compounds of Formula V

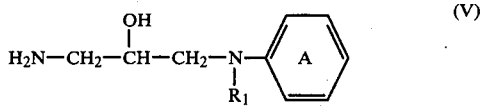

wherein $R_1$ and A are as defined above can be reacted with an optionally substituted benzoylchloride to obtain compounds of Formula VI

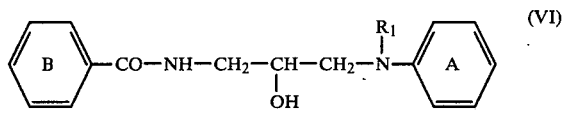

wherein A, B and $R_1$ are as defined above.

The starting materials of Formula V can be prepared in the manner described by M. Chadwick et al in J. Med. Chem. 9, Page 874 (1966).

At this reaction stage, compounds of Formula VI wherein $R_1$ represents hydrogen can subsequently be alkylated in conventional manner into the corresponding N-alkyl compounds. This alkylation can be carried out for example according to the methods of reductive carbonyl-amination which are known in the art such as the Leuckart-Wallach or the Eschweiler-Clarke reaction (see H. Krauch, W. Kunz, Reaktionen der Organischen Chemie (1976) page 126 and 131) or by alkylation with dialkylsulfates (see Houben-Weyl XI/1 (1957), S. 207 ff).

The compounds of Formula VI which are obtained in the above-described manner can subsequently be cyclized by reaction with phosphoroxyhalogenides, preferably phosphoroxychloride in conventional manner for example as is known from German Offenlegungsschrift Nos. 2 221 558, 2 314 993 and 2 520 937. Suitably the compounds of Formula VI or acid addition salts thereof are treated with a cyclizing agent at a temperature of between about 100° C. and 150° C. as is disclosed in German Offenlegungsschrift No. 2 520 937 and subsequently the resulting mixture of the two isomer compounds of Formula VII and Formula VIII

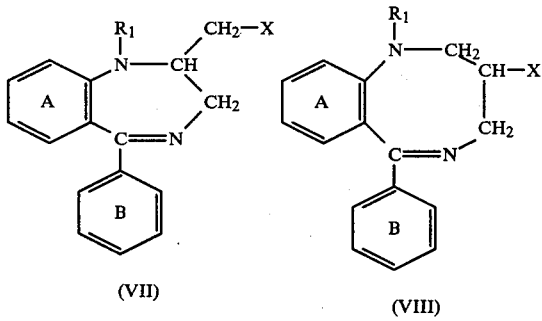

wherein A and B and $R_1$ are as defined above and X represents halogen, preferably chloride, is isolated.

The two isomeric compounds of Formula VII and Formula VIII are present in the reaction mixture in varying proportions depending on the type of substituents in the aromatic nuclei A and B as well as on the position of such substituents. This, however, is of no importance for the subsequent reaction of this mixture since both isomers yield compounds of Formula II wherein A, B, $R_1$ and $R_2$ are as defined above in the subsequent reaction step (see also Milkowski et al. Eur. J. Med. Chem. 6, page 501-507 (1976)). Therefore, no time consuming separation or analysis of the mixture of isomers is necessary.

Thus after roughly removing by-products yet without separation into the isomeric components, the mixture of isomeric compounds of Formula VII and Formula VIII which is obtained as described above can be reacted with an alkali metal imide, preferably potassiumphthalimide, in the manner described in German Offenlegungsschrift No. 2 353 187 for compounds of the type of Formula VII to obtain 2-phthalimido compounds of Formula IX

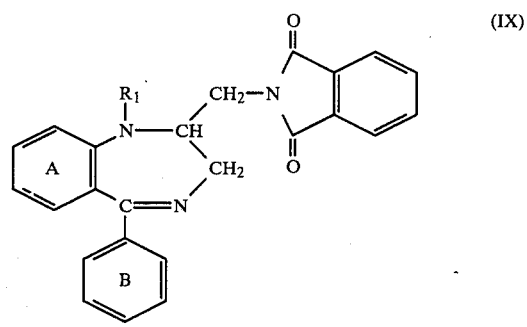

wherein A, B and $R_1$ are as defined above. The raw or optionally previously purified compound of Formula IX than can be split in a conventional manner by reaction with hydrazine hydrate or with diluted hydrochloric acid to obtain compounds of Formula II wherein A, B and $R_1$ are as defined above and $R_2$ is hydrogen (see H. Krauch, W. Kunz, Reaktionen der Organischen Chemie (1976), page 638). Suitably the preparation of the 2-phthalimido compound of Formula IX takes place in a solvent such as methanol, ethanol, isopropanol, dioxane, or dimethylformamide with or without addition of potassium iodide as catalyst at temperatures of from about 50° to about 130° C.

The splitting reaction of compounds of Formula IX into compounds of Formula II wherein $R_2$ is hydrogen suitably is carried out in a lower alkyl alcohol such as methanol, ethanol, isopropanol, t-butanol or water at temperatures of from about 20° to about 120° C., preferably at the boiling temperature of the solvent.

The mixture of isomeric compounds of Formula VII and Formula VIII also can be transformed into compounds of Formula II wherein $R_2$ in addition to hydrogen also may have the above-given meaning other than hydrogen by reacting the isomeric mixture with ammonium hydroxide whereby compounds of Formula II wherein $R_2$ is hydrogen are obtained or with a suitable primary amine such as, for example, methylamine, ethylamine, propylamine, butyamine, allylamine, or cyclopropylmethylamine to obtain compounds of Formula II wherein $R_2$ has a meaning other than hydrogen. The reaction can be carried out as is described in German Offenlegungsschrift No. 2 221 558 for compounds of the type of Formula VII with or without a solvent at normal atmospheric pressure or at elevated pressure at temperatures of from about 20° to about 150° C. Suitably an excess of amine may serve as a solvent for the reaction, yet inert solvents such as water, methanol, ethanol, isopropanol, t-butanol, dioxane, benzene, toluene, xylene may also be used.

According to a modification of the above reaction instead of ammonium hydroxide or of a primary amine an alkali metal salt thereof is reacted with the mixture of isomeric compounds of Formula VII and Formula VIII. Suitable metals are in particular lithium and sodium. Suitably an excess of ammonia or of the corresponding primary amines serve as inert solvent. Yet other inert solvents such as tetrahydrofurane, dioxane, benzene, and toluene also can be used. The alkali metal salts may be formed in situ or may be added in solid form. Suitable temperatures for the reaction are from about −50° to about 150° C.

According to the novel embodiment of the preparation of compounds of Formula I wherein A, B, $R_1$ and $R_2$ are as defined above according to the present innvention, compounds of Formula VII and/or Formula VIII are reacted with an alkali metal azide, preferably sodium or potassium azide to obtain 2-azidomethyl-1,4-benzodiazepine derivatives of Formula X

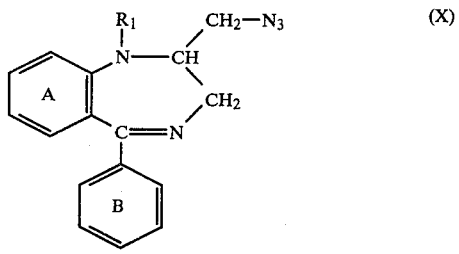

wherein A, B and $R_1$ are as defined above. Suitably the reaction takes place in an inert solvent at a temperature of from about −30° to 150° C. The compounds of Formula X can be isolated in the form of the free bases or in the form of acid addition salts thereof. Yet the compounds also may be subjected to further reaction without separation from the reaction mixture optionally after removal of the solvent.

Examples of suitable solvents for the preparation of the azides of Formula X include methylenechloride, chloroform, tetrahydrofurane, dioxane, dimethylformamide, dimethylsulfoxide, hexamethylphosphortriamide, methanol, ethanol, t-butanol, acetone, or methylisobutylketone.

The compounds of Formula X are novel compounds which provide valuable intermediates for the preparation of compounds of Formula I. Furthermore, the compounds of Formula X themselves also possess valuable pharmacological properties. In particular, the compounds of Formula X according to the present invention possess psycho pharmacological activities which have been demonstrated in standard screening tests of PANLABS Inc. in comparison with meprobramate and chlorodiazepoxide. The compounds further possess bronchodilatory properties which have been demonstrated in guinea pig lungs through which a flow of compound solution is passed in comparison with aminophyllin, and antiarrhythmic properties which are demonstrated after chloroform-induced arrhythmia in the mouse heart in comparison to chinidine.

The pharmacological tests gave satisfactory results in a dosage range of from about 0.5 to about 100 mg/kg. Accordingly, the compounds of Formula X of the present invention are therapeutically useful as sedatives, broncholytic agents and antiarrhythmic agents.

By subsequent splitting of these compounds in known manner by reaction with hydrazine hydrate/Raney-nickel with basic catalyzation or with propanedithiol 2-aminomethyl-1,4-benzodiazepine compounds of Formula II wherein $R_2$ is hydrogen are obtained. The reduction with hydrazine suitably is carried out in an alcohol such as methanol or ethanol under addition of a tertiary amine such as triethylamine at room temperature. The reduction with propanedithiol suitably is carried out by using methanol, ethanol, dimethylformamide or pyridine/water as a solvent.

The 2-aminomethyl compounds can be transformed into the desired 2- acylaminomethyl-1,4-benzodiazepine derivatives of Formula I as has been described above.

It is especially noted at this point that for the above-described reactions for the preparation of compounds of Formula II, IX and X the mixture of isomeric compounds of Formula VII and VIII suitably is used yet that it is evident to anyone skilled in the art that the mixture of isomers also can be separated into its components which later can separately be converted into compounds of Formula II, IX and X according to the above-described reaction.

Subsequent substitution of the nucleus A of the 1,4-benzodiazepine system by halogen or nitro substituents is possible in a conventional manner as has already been described in German Offenlegungsschrift No. 2 221 558. Such substitution suitably can be effected on compounds of Formula I, VII, IX and X. N-chlorosuccinimide or N-bromosuccinimide may for example serve as a halogenating agent.

For introducing the nitro substituent conventional nitrating agents can be used such as $KNO_3$ in $H_2SO_4$ or copper-II-nitrate-trihydrate in acetic acid anhydride.

Starting materials of Formula II wherein $R_1$ is hydrogen with the exception of those wherein A and/or B are substituted by alkyloxy or alkylthio may also be prepared by dealkylating a compound of Formula II wherein $R_1$ is alkyl, preferably methyl, by reaction with hydrogeniodide acid. The reaction is carried out in concentrated hydrogeniodide acid at temperatures of between about 50° and about 100° C.

The compounds of Formula I which are obtained by the processes according to the present invention may be isolated in the form of the free bases or, if desired, may be converted into acid addition salts with inorganic or organic acids in conventional manner. For example, in order to obtain the salt, the desired acid is added to a solution of the compound of Formula I in a suitable solvent. Preferably, an organic solvent is used wherein the resulting salt is unsoluble so that it can be separated by filtration. Examples of such solvents include ethanol, isopropanol, ether, acetone, acetic acid ethyl ester, acetone/ether, acetone/ethanol, ethanol/ether.

The following examples are intended to illustrate the preparation of the novel compounds of Formula I and of pharmaceutical compositions thereof as well as of the novel intermediate compounds of Formula X but are not intended to limit the scope of the present invention in any way.

The chemical structure of the novel compounds has been verified by spectroscopic analysis, in particular by exact analysis of the NMR-spectra. In the following table the melting points of the monohydrochlorides of the compounds are given where no other data are recited. The presence of any included amounts of water, acetone, ethanol or the like is noted.

Where no salt is given, the amide—C=O band in the IR spectrum of the oily base in the range of 1630–1650 cm$^{-1}$ is determined (Perkin-Elmer IR spectrophotometer 157 G).

EXAMPLE 1

1-methyl-2-[(thiophene-2-carbonyl)-aminomethyl]-5-phenyl-1H-2,3-dihydro-1,4-benzodiazepine (a) A mixture of 202 g of $N_1$-benzoyl-$N_2$-methyl-$N_2$-phenyl-2-hydroxy-1,3-diaminopropane and 1000 ml of phosphoroxychloride is heated under reflux for a period of 2.5 hours. Subsequently the excess phosphoroxychloride is distilled off and the residue is dissolved in 1000 ml of chloroform. The chloroform solution is agitated with 1000 ml of ice/water, the organic phase is separated and is washed five to six times with 200 ml of water each. Subsequently the organic phase is agitated with 1200 ml of sodium hydroxide solution (20%) and then washed with water until neutral reaction. The chloroform phase then is dried and decolorized by addition of sodium sulfate and γ-aluminum oxide (aluminum oxide "Giulini"). After filtering the solution is evaporated.

(b) The resulting oilybase (202 g) which comprises a mixture of 1-methyl-2-chloromethyl-5-phenyl-1H-2,3-dihydro-1,4-benzodiazepine and 1-methyl-3-chloro-6-phenyl-1,2,3,4-tetrahydro-benzodiazocine is introduced into 1300 ml of methanol, 138.5 g of potassium phthalimide and 38.2 g of potassium iodide are added and the mixture is heated under refluxed for 22 hours. Subsequently, the methanol is distilled off and 500 ml of chloroform are added to the residue. Insoluble components are filtered off and discarded. The filtrate is separated and 256.4 g of 1-methyl-2-phthalimidomethyl-5-phenyl-1H-2,3-dihydro-1,4-benzodiazepine are obtained in the form of an oily residue.

Without any further purification, this residue is added to 71.1 g of hyrazine hydrate in 3200 ml of ethanol and the reaction mixture is heated under reflux for 4.5 hours. Then 330 ml of concentrated hydrochloric acid (32%) are added and the reaction mixture is further heated under reflux for an additional 15 minutes. After cooling the formed crystals are filtered off. The filtrate is subsequently evaporated under vacuum. 1500 ml of water are added to the residue and the mixture is again filtered. Hydrochloric acid is added to the filtrate and, any non basic components are removed from the mixture by agitating with methylene chloride. The acid aqueous phase is rendered alkaline by addition of concentrated sodium hydroxide solution (50%). The base which separates in the form of an oil is dissolved in methylenechloride. The solution is washed several times with sodium chloride solution (10%), dried over sodium sulfate and filtered.

After distilling off the solvent, 127.3 g of residue are obtained and are dissolved in ether and filtered. A saturated solution of hydrogen chloride in ether is added to the filtrate. The formed crystals are filtered off, washed with ether and are stirred with cold acetone containing a small amount of isopropanol. The crystals are filtered off under suction, washed with acetone and dried.

108.5 g of 1-methyl-2-aminomethyl-5-phenyl-1H-2,3-dihydro-1,4-benzodiazepine dihydrochloride having a melting point of 209° to 213° C. are obtained.

(c) 13.4 g of 1-methyl-2-aminomethyl-5-phenyl-1H-2,3-dihydro-1,4-benzodiazepine (obtained as described above) and 7.65 ml of triethylamine are dissolved in 320 ml of methylene chloride. Under cooling and agitation with ice a solution of 8.12 g of thiophen-2-carboxylic acid chloride in 20 ml of methylene chloride is added. Subsequently, the reaction solution is allowed to stand at room temperature over night. Then the solution is washed with water, sodium carbonate solution (10%) and saturated sodium chloride solution, is dried over sodium sulfate and filtered. After distilling off the solvent 21 g of material are obtained and purified, chromotographically, using 300 g of aluminum oxide activity level I (standard Merck) as absorbent and eluating successively with cyclohexane, toluene, methylene chloride and ethanol. The toluene- and methylene chloride eluate (19.4 g) are added to each other and dissolved in ether. A solution of 7.8 g of racemic tartaric acid in ethanol is added. The tartrate is precipitated by addition of ether and after filteration is recrystallized from ethanol at a temperature of −70° C. to −60° C.

10 g of 1-methyl-2-[(thiophene-2-carbonyl)aminomethyl]-5-phenyl-1H-2,3-dihydro-1,4-benzodiazepine tartrate×0.4 mol of ethanol having a melting point of 110° to 125° C. (decomposition) are obtained. The free base has a melting point of 112°–115° C.

EXAMPLE 2

1-methyl-2-[(thiophene-3-carbonyl)-aminomethyl]-5-phenyl-1H-2,3-dihydro-1,4-benzodiazepine (a) A mixture of 68.4 g of the cyclization mixture obtained according to Example 1 (a) and containing 1-methyl-2-chloromethyl-5-phenyl-1H-2,3-dihydro-1,4-benzodiazepine and 1-methyl-3-chloro-6-phenyl-1,2,3,4-tetrahydro-benzodiazocine, 47.2 g of sodium azide and 420 ml of dimethylformamide is heated to 100° C. for a period of 4 hours. Subsequently, the dimethylformamide is distilled off under vacuum and 300 ml of toluene and 200 ml of water are added to the residue. The organic phase is separated, washed with sodium chloride solution (10%), dried over sodium sulfate and filtered. The solvent is distilled off and 56.1 g of raw product are obtained as residue. The residue is dissolved in ether and a saturated solution of hydrogen chloride in ether is added. The precipitated crystals are filtered off and are recrystallized from acetone/isopropanol.

36.7 g of 1-methyl-2-azidomethyl-5-phenyl-1H-2,3-dihydro-1,4-benzodiazepine hydrochloride having a melting point of 181°–183° C. are obtained.

(b) 21.7 g of 1-methyl-2-azidomethyl-5-phenyl-1H-2,3-dihydro-1,4-benzodiazepine hydrochloride are dissolved in 325 ml of methanol. 9.5 ml of triethylamine and subsequently 13.5 ml of hydrazine hydrate are added. Then 10 g of Raney-nickel are added portionwise to the reaction solution under agitation at room temperature. After three hours, the addition of Raney-nickel is completed The reaction mixture is agitated for another one hour, then the Raney-nickel is filtered off. The filtrate is evaporated under vacuum, the residue is dissolved in methylene chloride and the solution is washed with water and sodium chloride solution (10%). Subsequently, the organic phase is dried over sodium sulfate, filtered and evaporated. 17.1 g of 1-methyl-2-aminomethyl-5-phenyl-1H-2,3-dihydro-1,4-benzodiazepine are obtained. Its dihydrochloride has a melting point of 209° to 213° C.

(c) 13.5 g of thiophene-3-carboxylic acid are dissolved in 300 ml of methylene chloride and are cooled to a temperature of 0° to 5° C. Then 14.5 ml of triethylamine are added and subsequently 11.2 ml of chloroformic acid ethyl ester are added dropwise within a period of 5 to 10 minutes. Then the reaction solution is agitated for another 30 minutes at the temperature of 0° to 5° C. and subsequently is added dropwise and under cooling to a solution of 27.9 g of 1-methyl-2-aminomethyl-5- phenyl-1H-2,3-dihydro-1,4-benzodiazepine in 200 ml of methylene chloride in such a manner that the temperature is retained at between 0° to 5° C. Subsequently, the reaction solution is agitated for another four hours at room temperature, then is washed with water, diluted ammonium hydroxide solution (10%) and sodium chloride solution, dried over sodium sulfate and filtered. The solvent is distilled off. 37.8 g of raw product are obtained.

The raw base is dissolved in ether and a saturated solution of hydrogen chloride in ether is added. The precipitated crystals are filtered off and are heated to boiling temperature in a mixture of acetone/acetic acid ethyl ester. 21.9 g of 1-methyl-2-[(thiophene-3-carbonyl)-aminomethyl]-5-phenyl-1H-2,3-dihydro-1,4-benzodiazepine hydrochloride having a melting point of 234°–237.5° C. are obtained.

EXAMPLE 3

7-nitro-1-methyl-2-[(thiophene-2-carbonyl)-aminomethyl]-5-phenyl-1H-2,3-dihydro-1,4-benzodiazepine 2.5 g of 1-methyl-2-[(thiophene-2-carbonyl)-aminomethyl]-5-phenyl-1H-2,3-dihydro-1,4-benzodiazepine are dissolved in 9 ml of acetic acid anhydride. 1.58 g of copper (II)-nitrate.3H$_2$O are added portionwise at a temperature of 30°–35° C. After addition of the copper salt is completed, the reaction mixture is added to a saturated sodium bicarbonate solution and ice. The alkaline solution is extracted with 50 ml of methylene chloride and the organic phase is worked up in a conventional manner.

The free base is transferred into the hydrochloride. 0.7 g 7-nitro-1-methyl-2-[(thiophene-2-carbonyl)-aminomethyl]-5-phenyl-1H-2,3-dihydro-1,4-benzodiazepine hydrochloride having a melting point of 254°–256° C. are obtained.

EXAMPLE 4

7-nitro-1-methyl-2-[(thiophene-2-carbonyl)aminomethyl]-5-phenyl-1H-2,3-dihydro-1,4-benzodiazepine A solution of 4.5 g of potassium nitrate in 8 ml of concentrated sulfuric acid is added at a temperature of 5° C. to a solution of 5.2 g of 1-methyl-2-chloromethyl-5-phenyl-1H-2,3-dihydro-1,4-benzodiazepine in 50 ml of glacial acetic acid. The reaction mixture is agitated at room temperature for a period of one hour and then is poured onto 200 g of ice, is rendered alkaline by addition of diluted sodium hydroxide solution (20%) and is extracted with methylene chloride. Subsequently, the organic phase is washed with water until neutral reaction, is dried over sodium sulfate and filtered. After distilling off the solvent, 7-nitro-1-methyl-2-chloromethyl-5-phenyl-1H-2,3-dihydro-1,4-benzodiazepine is obtained. Its hydrochloride having a melting point of 230°–240° C.

A mixture of 4.5 g of this compound, 50 ml of methanol and 2.7 g of potassium phthalimide and 800 mg of potassium iodide is heated under reflux. After the reaction mixture has been worked up in conventional manner, 4 g of 7-nitro-1-methyl-2-phthalimidomethyl-5-phenyl-1H-2,3-dihydro-1,4-benzodiazepine are obtained. These are heated under reflux in 200 ml of hydrochloric acid (24%) for a period of four hours. The reaction solution is partially evaporated and sodium hydroxide solution is carefully added until an alkaline reaction is reached. Then the raw reaction product (2 g of 7-nitro-1-methyl-2-aminomethyl-5-phenyl-1H-2,3-dihydro-1,4-benzodiazepine) is extracted with methylene chloride and isolated in a conventional manner. Without further purification, it is dissolved in 100 ml of methylene chloride and 0.65 g of triethylamine and subsequently under cooling with ice, a solution 0.93 g of thiophene-2-carboxylic acid chloride in 20 ml of methylene chloride are added. After the reaction mixture has been worked up in conventional manner, 1.8 g of 7-nitro-1-methyl-2-[(thiophene-2-carbonyl)-aminomethyl]-1H-2,3-dihydro-1,4-benzodiazepine hydrochloride having a melting point of 254°–256° C. are obtained.

EXAMPLE 5

7-chloro-1-methyl-2-[(furane-2-carbonyl)-aminomethyl]-5-phenyl-1H-2,3-dihydro-1,4-benzodiaepine The mixture of 4.2 g of 1-methyl-2-chloromethyl-5-phenyl-1H-2,3-dihydro-1,4-benzodiazepine and 1.95 g of N-chlorosuccinimide in 75 ml of methylenechloride is heated under reflux for a period of 24 hours. Then the reaction solution is washed with water and dried over sodium sulfate. After filtering and distilling off the solvent, 4.5 g of 7-chloro-1-methyl-2-chloromethyl-5-phenyl-1H-2,3-dihydro-1,4-benzodiazepine are obtained. Its hydrochloride has a melting point of 110°–112° C. (from isopropanol).

A mixture of 4.0 g of this compound, 25 ml of methanol, 2.5 g of potassium phthalimide and 750 mg of potassium iodide is heated under reflux for 20 hours. Then the methanol is distilled off and 25 ml of chloroform are added to the residue. The insoluble components are filtered off and discarded. The filtrate is evaporated and 6.3 g of residue are obtained. A mixture of residue, 1.9 g of hydrazine hydrate and 100 ml of ethanol is heated under reflux for a period of four hours. Then 10 ml of concentrated hydrochloric acid (32%) are added and the reaction mixture is again heated under reflux for another 15 minutes. After cooling the precipiated crystals are filtered off and the filtrate is evaporated under vacuum. 50 ml of water are added to the residue and the mixture is again filtered. The filtrate is acidified with concentrated hydrochloric acid and is extracted with methylenechloride (100 ml). The base is separated in the form of an oil by addition of concentrated sodium hydroxide solution (50%) and is dissolved in methylenechloride. The solution is washed with saturated sodium chloride solution, dried over sodium sulfate and filtered. The solvent is distilled off and 3.1 g of 7-chloro-1-methyl-2-aminomethyl-5-phenyl-1H-2,3-dihydro-1,4-benzodizepine are obtained. This residue is dissolved in 80 ml of ethylenechloride without further purification and 1.05 g of triethylamine are added. Then a solution of 1.35 g of furan-2-carboxylic acid chloride in 10 ml of methylenechloride is added dropwise under cooling with ice and exclusion of moisture. Then the reaction mixture is agitated at room temperature for another two hours and is worked up in a conventional manner. The free base is transformed into its hydrochloride. 2.67 g of 7-chloro-1-methyl-2-[(furane-2-carbonyl)-aminomethyl]-5-phenyl-1H-2,3-dihydro-1,4-benzodiazepine hydrochloride having a melting point of 235°–236.5° C. are obtained.

EXAMPLE 6

1-methyl-2-[(furane-3-carbonyl)-aminomethyl]-5-(2'-fluorophenyl)-1H-2,3-dihydro-1,4-benzodiazepine 12.5 g of 1-methyl-2-aminomethyl-5-(2'-fluorophenyl)-1H-2,3-dihydro-1,4-benzodiazepine dihydrochloride are dissolved in 160 ml of methylenechloride under addition of 15.9 ml of triethylamine. Then a solution of 5.0 g of furan-3-carboxylic acid chloride in 50 ml of methylene chloride is added dropwise under ice cooling. The reaction solution is agitated for 3 hours at room temperature and then is worked up in a conventional manner. 9.0 g of the hydrochloride of the title compound having a melting point of 227°–228° C. are obtained.

EXAMPLE 7

8-methoxy-1-methyl-2-[(1-methylpyrrol-2-carbonyl)-aminomethyl]-5-(2'-chlorophenyl)-1H-2,3-dihydro-1,4-benzodiazepine.

9.2 g of 8-methoxy-1-methyl-2-aminomethyl-5-(2'-chlorophenyl)-1H-2,3-dihydro-1,4-benzodiazepine are dissolved in 230 ml of methylenechloride and 4 ml of triethylamine are added. Then a solution of 4.0 g of 1-methylpyrrol-2-carboxylic acid chloride in 25 ml of methylenechloride are added dropwise under ice cooling. After the addition is completed, the reaction mixture is immediately worked up in a conventional manner. 2.4 g of the hydrochloride of the title compound are obtained which contain 0.66 mol $H_2O$ and possess a melting point of 178°–225° C. (decomposition).

EXAMPLE 8

2-[(thiophene-2-carbonyl)-aminomethyl]-5-phenyl-1H-2,3-dihydro-1,4-benzodiazepine A mixture of 10 g of 1-methyl-2-aminomethyl-5-phenyl-1H-2,3-dihydro-1,4-benzodiazepine and 40 ml of hydrogen iodide acid (67%) is heated to a temperature at 80° C. under agitation for a period of four hours. Subsequently, the reaction liquid is poured onto ice (500 g) and is carefully neutralized by addition of solid sodium carbonate. After adding 50 ml of concentrated sodium hydroxide solution the base is extracted with methylenechloride. The organic phase is washed with saturated sodium chloride solution, dried over sodium sulfate and filtered. The solvent is distilled off and 9 g of 2-aminomethyl-5-phenyl-1H-2,3-dihydro-1,4-benzodiazepine are obtained as an oily base. The oily base is dissolved in 250 ml of methylenechloride under addition of 3.6 g of triethylamine. A solution of 5.2 g of thiophene-2-carboxylic acid chloride in 25 ml of methylenechloride is added dropwise under agitation and cooling. The reaction solution is agitated for two hours at room temperature and then is worked up. 20 g of oily residue are obtained which is purified chromotographically using 200 g of aluminum oxide activity degree II as absorbent and eluating with toluene. The eluate is collected in 200 ml fractions. The desired reaction product is enriched in fractions 10 to 24. After evaporating the toluene, these fractions together are dissolved in 200 ml of methylene chloride. The methylenechloride solution is stirred with 50 g of γ-aluminum oxide and filtered. The filtrate is evaporated and 14.2 g of raw product are obtained as residue and are recrystallized from toluene. 6.7 g of the title base having a melting point of 172°–174° C. are obtained.

EXAMPLE 9

1-methyl-2-[(thiophene-2-carbonyl)-N-methylaminomethyl]-5-phenyl-1H-2,3-dihydro-1,4-benzodiazepine 7.6 g of 1-methyl-2-[(thiophene-2-carbonyl)aminomethyl]-5-phenyl-1H-2,3-dihydro-1,4-benzodiazepine are dissolved in 100 ml of tetrahydrofurane and 0.66 g of sodium hydride (80% in oil) are added under agitation. Then the reaction mixture is cooled to 5° C. and a solution of 1.36 ml of methyliodide in 10 ml of tetrahydrofurane is added slowly (about 30 minutes are used for the dropwise addition). Subsequently, the reaction solution is agitated for two hours at a temperature of 5° to 10° C. and then is diluted with 10 ml of ice water in such an amount of toluene that after addition of more water two phases are formed. The organic phase is washed with water several times, dried over sodium sulfate and filtered. The solvent is distilled off and 7.5 g of raw product are obtained.

The raw product is dissolved in 50 ml of ether and a separated solution of 7.8 g of D,L-tartaric acid in ethanol is added. By further addition of ether the tartrate is precipitated and is filtered off and recrystallized from ethanol.

9 g of 1-methyl-2-[(thiophene-2-carbonyl)-N-methylaminomethyl]-5-phenyl-1H-2,3-dihydro-1,4-benzodiazepine tartrate×0.4 mol of ethanol having a melting point of 110°–125° C. are obtained.

EXAMPLE 10

1-methyl-2-[(thiophene-2-carbonyl)-N-n-propylaminomethyl]-5-phenyl-1H-2,3-dihydro-1,4-benzodiazepine A mixture of 10 g of the product which is obtained by cyclization with phosphoroxychloride from $N_1$-benzoyl-$N_2$-methyl-$N_2$-phenyl-2-hydroxy-1,3-diaminopropane according to Example 1 (a) and 100 ml of n-propylamine is heated in an autoclave to a temperature of 80° C. for a period of 24 hours. After cooling the excess amine is distilled off. Water and subsequently 50 ml of diluted sodium hydroxide solution (20%) are added to the residue and the mixture is extracted with methylenechloride. The organic phase is washed with saturated sodium chloride solution, dried over sodium sulfate and filtered. The solvent is distilled off and 8 g of 1-methyl-2-propylaminomethyl-5-phenyl-1H-2,3-dihydro-1,4-benzodiazepine is obtained as an oily residue.

This residue is dissolved in 150 ml of methylenechloride under addition of 2.6 g of triethylamine. A solution of 3.8 g of thiophene-2-carboxylic acid chloride in 20 ml of methylenechloride is added under agitation and cooling with ice. The reaction solution is agitated at room temperature for two hours and then is washed with water, sodium carbonate solution (10%) and saturated sodium chloride solution. After drying over sodium sulfate and filtration the solvent is distilled off. The residue (9 g) is dissolved in ethanol, 2 mol of racemic-tartaric acid are added and the product is crystallized from ethanol/ether. 7 g of the free base are obtained which crystallize with 1.6 mol of tartaric acid and 0.5 mol of $H_2O$. Melting point 108°–118° C. (decomposition).

According to Examples 1 to 10, the following compounds can be prepared:

1-methyl-2-[(thiophene-2-carbonyl)-aminomethyl]-5-phenyl-1H-2,3-dihydro-1,4-benzodiazepine derivatives of Formula I wherein A, B are substituted and $R_4$ is defined as follows:

| A | B | $R_4$ | Melting Point °C. Hydrochloride |
|---|---|---|---|
| H | H | H | 112–115 (Base) |

-continued

| A | B | R$_4$ | Melting Point °C. Hydrochloride |
|---|---|---|---|
| 8-Cl | H | H | 240–242 1.5 HCl |
| 7-F | H | H | 224–227 |
| 8-F | H | H | 232–236 |
| 7-CH$_3$ | H | H | 219–224 |
| 6,8-di-CH$_3$ | H | H | 232–234 |
| 7,8-di-CH$_3$ | H | H | 246–249 |
| 8-C$_2$H$_5$ | H | H | 221–223.5 |
| 7-i-C$_3$H$_7$ | H | H | 262–264 |
| 7-OCH$_3$ | H | H | 150–157 . 0.5 H$_2$O |
| 8-OCH$_3$ | H | H | 230.5–231.5 |
| 7,8-di-OCH$_3$ | H | H | 243–245 |
| 6,8-di-OCH$_3$ | H | H | 245–246.5 |
| 8-OC$_2$H$_5$ | H | H | 195–197 . 1 acetone |
| 7-n-OC$_3$H$_7$ | H | H | 227–230 1.4 HCl |
| 7,8-OCH$_2$O— | H | H | 259–263 |
| 7,8-OC$_2$H$_4$O— | H | H | 265–276 |
| 8-SCH$_3$ | H | H | 259–265 |
| H | 2-F | H | 241–242 |
| H | 3-OCH$_3$ | H | 205–208 |
| H | 2,6-di-OCH$_3$ | H | 202–205 |
| H | 3,4-di-OCH$_3$ | H | 218–220 |
| 7-CH$_3$ | 2-F | H | 238–249 |
| 8-OCH$_3$ | 3-F | H | 236–238 |
| 8-OCH$_3$ | 4-F | H | 226–229 |
| 8-OCH$_3$ | 2-F | H | 213–216 |
| 8-OCH$_3$ | 2-Cl | H | 220–229 |
| 8-OCH$_3$ | 2-Br | H | 229–232 |
| 8-OCH$_3$ | 2-CF$_3$ | H | 173–177 |
| 8-OCH$_3$ | 3-CF$_3$ | H | 224–227 |
| 8-OCH$_3$ | 4-CF$_3$ | H | 224–227 |
| 8-OCH$_3$ | 2-CH$_3$ | H | 229–232 |
| 7-F | 3,4,5-tri-OCH$_3$ | H | 201–203 |
| 7-CH$_3$ | 3,4,5-tri-OCH$_3$ | H | 178–182 |
| 7-Br | 2-Cl | H | 246–247.5 |
| 7-CF$_3$ | H | H | 254–256 |
| 7,8-OCH$_2$O— | 2-F | H | 199–201 (Base) |
| H | H | 5-C$_2$H$_5$ | 192–195 |
| 8-OCH$_3$ | 2-F | 5-C$_2$H$_5$ | 171–174 |
| H | H | 4-CH$_3$ | 221–223 . 0.75 acetone |
| H | H | 3-CH$_3$ | 227–228 |
| 8-OCH$_3$ | H | 3-CH$_3$ | 226–227 |
| 7-n-OC$_3$H$_7$ | H | 3-CH$_3$ | 186–189 |
| 8-OCH$_3$ | 2-F | 3-CH$_3$ | 161–165 . 0.5 H$_2$O |
| 8-OCH$_3$ | 2-F | 5-CH$_3$ | 180–189 (decomp.) . 0.25 H$_2$O |
| 8-OCH$_3$ | 2-F | 4-CH$_3$ | 198–202 . 0.15 H$_2$O |
| H | H | 4-Br | 202–205 |
| H | H | 5-Br | 236–245 |
| 8-OCH$_3$ | H | 5-Br | 225–226 |
| 8-OCH$_3$ | 2-F | 5-Br | 219.5–220.5 |
| 8-OCH$_3$ | 3-F | 5-Br | 221–222 |
| 8-OCH$_3$ | 4-F | 5-Br | 228–231 |
| H | H | 5-CH$_3$ | 218–223 . 0.4 Acetone |
| 8-F | H | 5-CH$_3$ | 238–240 |
| 7-OCH$_3$ | H | 5-CH$_3$ | 246–251 |
| 8-OCH$_3$ | H | 5-CH$_3$ | 231–233 |
| 8-OC$_2$H$_5$ | H | 5-CH$_3$ | 238–240 |
| 7,8-OCH$_2$O— | H | 5-CH$_3$ | 257–267 |
| 8-SCH$_3$ | H | 5-CH$_3$ | 229–232 |
| 7-CH$_3$ | 2-F | 5-CH$_3$ | 238–247 |
| 7-F | 3,4,5-OCH$_3$ | 5-CH$_3$ | 170–172 |
| H | H | 5-OCH$_3$ | Oil |
| H | H | 5-OC$_2$H$_5$ | Oil |
| H | H | 5-Cl | Oil |
| 8-OCH$_3$ | 4-F | 5-CH$_3$ | Oil |
| 8-OCH$_3$ | 4-F | 4-CH$_3$ | Oil |
| 7,8-OCH$_2$O— | 2-F | 5-CH$_3$ | 228–243 |
| 7,8-OCH$_2$O— | 2-F | 4-CH$_3$ | Oil |
| 7,8-OCH$_2$O— | 2-F | 5-OCH$_3$ | 218–223 |
| H | 2-F | 5-OCH$_3$ | Oil |

| A | B | R$_4$ | Melting Point °C. Hydrochloride |
|---|---|---|---|
| H | 2-F | 4-Br | 204–208 |

1-methyl-2-[(thiophene-3-carbonyl)-aminomethyl]-5-phenyl-1H-2,3-dihydro-1,4-benzodiazepine derivatives of Formula I, wherein A, and B are substituted and R$_4$ is defined as follows:

| A | B | R$_4$ | Melting Point °C. Hydrochloride |
|---|---|---|---|
| 7-CH$_3$ | H | H | 244–245.5 2 HCl |
| 6,8-di-CH$_3$ | H | H | 227–229 |
| 7,8-di-CH$_3$ | H | H | 245–247 |
| 8-C$_2$H$_5$ | H | H | 209–212 |
| 7-i-C$_3$H$_7$ | H | H | 247–252 |
| 7-OCH$_3$ | H | H | 127–130 1.34 HCl . 0.45 H$_2$O |
| 8-OCH$_3$ | H | H | 222–224 |
| 7,8-di-OCH$_3$ | H | H | 227–229 |
| 8-OC$_2$H$_5$ | H | H | 160–166 . 0.9 acetone |
| 7-n-OC$_3$H$_7$ | H | H | 227–230 |
| 7,8-OCH$_2$O— | H | H | 264–269 |
| 8-SCH$_3$ | H | H | 243–246 |
| H | 2-F | H | 242–243 |
| H | 3-OCH$_3$ | H | 205–207.5 |
| H | 3,4-di-OCH$_3$ | H | 216–217 |
| 7-Br | 2-Cl | H | 259–263 |
| 7-F | 3,4,5-tri-OCH$_3$ | H | 219–223 |
| 7-CH$_3$ | 3,4,5-tri-OCH$_3$ | H | 184–187 |
| H | 3-CF$_3$ | H | 231–232 |
| 8-OCH$_3$ | 4-OCH$_3$ | H | 218–222 |
| 7-Cl,8-OCH$_3$ | 2-F | H | Oil |
| 8-CH$_3$ | 2-F | H | 237–247 |
| 8-NO$_2$ | H | H | Oil |
| 8-OC$_2$H$_5$ | 2-F | H | 227–237 |
| 8-i-OC$_3$H$_7$ | 2-F | H | 222–226 |
| 7,8-OCH$_2$O— | 2-F | H | 164–168 (Base) |
| 6-OCH$_3$ | 2-F | H | Oil |
| 7-F,8-OCH$_3$ | 2-F | H | Oil |
| 6,7-OCH$_2$O— | 2-F | H | Oil |
| H | 2-F | H | Oil |
| H | 4-CF$_3$ | H | Oil |
| 6-OH | 2-F | H | Oil |
| 9-CH$_3$ | H | H | Oil |
| 8-CH$_3$ | H | H | 226–236 |
| H | H | 2-CH$_3$ | Oil |
| H | 2-F | 2-CH$_3$ | Oil |
| 8-CH$_3$,6-OCH$_3$ | 2-F | H | Oil |

1-methyl-2-[(furane-2-carbonyl)-aminomethyl]-5-phenyl-1H-2,3-dihydro-1,4-benzodiazepine derivatives of Formula I, wherein A and B are substituted and R$_4$ is defined as follows:

| A | B | R$_4$ | Melting Point °C. Hydrochloride |
|---|---|---|---|
| H | H | H | 222–225 |
| 7-CH$_3$ | H | H | 238–240 |
| 8-C$_2$H$_5$ | H | H | 217.5–219 |
| 7-i-C$_3$H$_7$ | H | H | 245–251 |
| 7-OCH$_3$ | H | H | 219–222 . 0.25 H$_2$O |
| 6,8-di-OCH$_3$ | H | H | 242–244 |
| 7,8-di-OCH$_3$ | H | H | 242.5–244 |
| 7,8-OCH$_2$O— | H | H | 258–265 |
| 8-SCH$_3$ | H | H | 246–249 |
| H | 2-F | H | 225–227 |
| H | 3-OCH$_3$ | H | 195–197 |
| H | 3,4-di-OCH$_3$ | H | 215–217 . 0.3 H$_2$O |
| 7-Br | 2-Cl | H | 237–239 |

-continued

| A | B | R4 | Melting Point °C. Hydrochloride |
|---|---|---|---|
| 7-F | 3,4,5-tri-OCH3 | H | 168-172 |
| 7-CH3 | 3,4,5-tri-OCH3 | H | 191-197 |
| 7,8-di-CH3 | H | H | 241-244 |
| 6,8-di-CH3 | H | H | 232.5-234 |
| H | H | 5-CH3 | 196-198 |
| 7,8-OCH2O— | 2-F | 5-CH3 | 246-259 |
| 8-OCH3 | H | H | 225-228 |
| 8-OCH3 | H | 5-CH3 | 228-230 |
| 7-n-OC3H7 | H | 5-CH3 | 216-219 |
| H | H | 5-NO2 | 199-200 (base) |

1-methyl-2-[(furane-3-carbonyl)-aminomethyl]-5-phenyl-1H-2,3-dihydro-1,4-benzodiazepine derivatives of Formula I, wherein A and B are substituted and R4 is as defined as follows:

| A | B | R4 | Melting Point °C. Hydrochloride |
|---|---|---|---|
| H | H | H | 135-137 (base) |
| 7-Cl | H | H | 251-253 1.1 HCl |
| 8-Cl | H | H | 229-231 |
| 7-F | H | H | 224-226 |
| 8-F | H | H | 235-236 |
| 7-CH3 | H | H | 224-226 |
| 7,8-di-CH3 | H | H | 243.5-247 |
| 6,8-di-CH3 | H | H | 231-232 |
| 8-C2H5 | H | H | 201-204 |
| 7-i-C3H7 | H | H | 243-246 . 0.2 H2O |
| 7-OCH3 | H | H | 132-138 1.5 HCl . 0.3 H2O |
| 8-OCH3 | H | H | 213-216 |
| 8-OC2H5 | H | H | 147-152 . 0.5 H2O . 0.5 Acetone |
| 7-n-OC3H7 | H | H | 214-218 |
| 7,8-di-OCH3 | H | H | 240-241.5 |
| 7,8-OCH2O— | H | H | 201-204 (Base) |
| 7,8-OCH2CH2O— | H | H | 267-275 |
| 8-SCH3 | H | H | 247-249 |
| H | 2-F | H | 227-228 |
| H | 3-CF3,4-Cl | H | 184-186 . 0.6 H2O . 0.3 Acetone |
| H | 3-OCH3 | H | 183-186 |
| H | 2,6-di-OCH3 | H | 198-202 |
| H | 3,4-di-OCH3 | H | 215-217 |
| 7-CH3 | 2-F | H | 236-243 1.4 HCl . 0.5 H2O |
| 8-OCH3 | 2-Cl | H | 220-222 . 0.2 ethylacetate |
| 8-OCH3 | 2-Br | H | 228-233 . 0.5 H2O |
| 8-OCH3 | 3-F | H | 234-236 |
| 8-OCH3 | 4-F | H | 229-232 |
| 8-OCH3 | 2-F | H | 220-221 |
| 8-OCH3 | 2-CF3 | H | 219-222 . 1,3 H2O |
| 8-OCH3 | 3-CF3 | H | 179-181 (Base) |
| 8-OCH3 | 4-CF3 | H | 231-232 . 0,7 H2O |
| 8-OCH3 | 2-CH3 | H | 211-214 |
| 8-OCH3 | 2,4-di-Cl | H | 229-233 |
| 7-F | 3,4,5,-tri-OCH3 | H | 218-221 |
| 7-CH3 | 3,4,5-tri-OCH3 | H | 164-167 |
| H | 2-CF3 | H | 199-201 |
| H | 2,6-di-F | H | 228-229 |
| H | 2-Br | H | 218-220 |
| H | 3-CF3 | H | 215-217 Or 194-195 |
| 8-OCH3 | 2-OCH3 | H | 206-209 |
| 8-OCH3 | 3-OCH3 | H | 216-219 |
| 8-OCH3 | 4-OCH3 | H | 230-233 |
| H | 4-CF3 | H | oil |
| 8-CH3 | 2-F | H | 214-223 |
| 8-OCH3 | 2,6-di-F | H | oil |
| 8-NO2 | H | H | oil |
| 8-OC2H5 | 2-F | H | 199-204 |
| 8-i-OC3H7 | 2-F | H | 183-186 |
| 7,8-OCH2O— | 2-F | H | 209-213 (Base) |
| 6-OCH3 | 2-F | H | Oil |
| 7-F,8-OCH3 | H | H | Oil |
| 8-OCH3 | 4-F | 2-CH3 | Oil |
| 8-OCH3 | 4-F | 5-CH3 | Oil |
| H | H | 2-CH3 | Oil |
| H | H | 5-CH3 | 188-192 X 0,7 Acetone |
| 8-i-OC3H7 | 2-F | 2-CH3 | Oil |
| 8-i-OC3H7 | 2-F | 5-CH3 | 191-195 |
| 7,8-OCH2O— | 2-F | 2-CH3 | Oil |
| 7,8-OCH2O— | 2-F | 5-CH3 | Oil |
| H | 2-F | 2-CH3 | Oil |
| H | 2-F | 5-CH3 | Oil |
| 8-CH3 | H | H | 234-243 |
| 8-CH3,6-OCH3 | 2-F | | Oil |
| 7-CH3,9-Cl | H | H | Oil |

R1-2-(R3-carbonyl-R2-aminomethyl)-5-phenyl-1H-2,3-dihydro-1,4-benzodiazepine derivatives of Formula I, wherein A and B are substituted, and R1, R2, R3 and R4 are defined as follows:

| R3 | R1 | R2 | R4 | A | B | | Melting Point °C. |
|---|---|---|---|---|---|---|---|
| Thiophene-2 | C2H5 | H | H | H | H | HCl | 238-241 |
| " | CH3 | C2H5 | H | H | H | Base | 115-117 |
| " | CH3 | C2H5 | H | 8-OCH3 | H | 1,2 HCl · 0.5 Acetone | 102-115 |
| " | CH3 | n-C3H7 | H | H | H | 1,6 Tartrate 0.5 H2O | 108-118 |
| " | CH3 | Allyl | H | H | H | Base | 112-114 |
| " | CH3 | CH3 | H | H | H | 1,4 Tartrate | 96-105 |
| Thiophene-3 | C2H5 | H | H | 8-OCH3 | 2,4-di-F | Base | Oil |
| " | C2H5 | H | 2-CH3 | 8-OCH3 | 2-F | HCl | 199-201 |
| " | C2H5 | H | 2-CH3 | H | 2-F | Base | Oil |
| " | C2H5 | H | H | H | H | HCl | 224.5-226.5 |
| " | C2H5 | H | H | 8-OCH3 | 2-F | HCl | 223-225 |
| " | Cyclopropyl-methyl | H | H | 8-OCH3 | H | Base | Oil |
| " | H | H | H | H | 2-F | Base | Oil |
| " | C2H5 | H | H | 8-OCH3 | 2,3-di-Cl | Base | Oil |
| Furane-3 | C2H5 | H | H | H | H | HCl . 0.15 H2O | 246-247 |
| " | C2H5 | H | H | 8-OCH3 | 2-F | HCl | 228-231 |
| " | n-C4H9 | H | H | 8-OCH3 | 2-F | HCl | 204-206 |
| " | CH3 | CH3 | H | 8-OCH3 | H | HCl | 186-189 |

-continued

| $R_3$ | $R_1$ | $R_2$ | $R_4$ | A | B | | Melting Point °C. |
|---|---|---|---|---|---|---|---|
| | $CH_3$ | $C_2H_5$ | H | 8-$OCH_3$ | H | 1,5-Tartrate | 95-110 |
| " | $CH_3$ | Allyl | H | 8-$OCH_3$ | H | Base | Oil |
| " | H | H | H | H | 2-F | Base | Oil |

1-methyl-2-($R_5$-2-carbonyl)-aminomethyl-5-phenyl-1H-2,3-dihydro-1,4-benzodiazepine derivatives of Formula I wherein A and B are substituted and $R_5$ is as defined as follows:

| A | B | $R_5$ | Melting Point °C. Hydrochloride |
|---|---|---|---|
| H | H | 1H-pyrrol | 224-229 |
| 8-$OCH_3$ | H | " | 234-235 |
| H | 2-F | " | 250-252 |
| 8-$CH_3$ | 2-F | " | Oil |
| 7,8-$OCH_2O$— | 2-F | " | 127-138 Base × 0.25 ether |
| 8-$OCH_3$ | 4-$OCH_3$ | " | 234-235 |
| H | H | 1-methylpyrrol | 232-238 |
| 8-$OCH_3$ | H | " | 233-235 |
| 8-$OCH_3$ | 2-Br | " | 176-191 (decomp.) . 0.4 $H_2O$. . 0.4 $C_2H_5OH$ |
| 8-$OCH_3$ | 2-$CH_3$ | " | 210-213 |
| 8-$OCH_3$ | 4-$OCH_3$ | " | 222-224 |
| 7,8-$OCH_2O$— | 2-F | " | 236-249 |
| H | 2-F | " | 174-184 |
| 8-$CH_3$ | 2-F | " | 166-169 × 0,5 acetone |
| 8-$CH_3$ | H | " | 217-229 × 0,4 acetone |
| H | H | 1,2-dimethylpyrrol | Oil |
| 7-n-$OC_3H_7$ | H | 1-methylpyrrol | 206-209 × 0,5 $H_2O$ |

1-methyl-2-($R_3$CO-aminomethyl)-5-phenyl-1H-2,3-dihydro-1,4-benzodiazepine derivatives of Formula I wherein A and B are substituted and $R_3CO$ is defined as follows:

| A | B | $R_3CO$ | Melting Point °C. Dihydrochloride |
|---|---|---|---|
| 8-$OCH_3$ | H | picolinoyl | 216-218 1.8 HCl |
| 7-Br | 2-Cl | " | 217.5-219 1 HCl |
| H | H | nicotinoyl | 211-214 . 0.13 $H_2O$ |
| 8-$OCH_3$ | H | " | 164-175 . 0.4 $H_2O$ . 0,83 acetone |
| 7-Br | 2-F | " | 245-248 |
| 7-Br | 2-Cl | " | 235-238 . 0.25 $H_2O$ |
| 7-Cl | 2-Cl | " | 231-233 |
| 8-$OCH_3$ | H | isonicotinoyl | 231-234 . 0.4 $H_2O$ |
| 7-Br | 2-Cl | " | 243-244 |

EXAMPLE 11

A mixture of 68.4 g of the cyclization mixture of 1-methyl-2-chloromethyl-5-phenyl-1H-2,3-dihydro-1,4-benzodiazepine and 1-methyl-3-chloro-6-phenyl-1,2,3,4-tetrahydro-benzodiazocine, 47.2 g of sodiumazide and 450 ml of dimethylformamide is heated to 100° C. for a period of four hours. Then the dimethylformamide is distilled off under vacuum and 300 ml of toluene and 200 ml of water are added to the residue. The organic phase is separated, washed with sodium chloride solution (10%), dried over sodium sulfate and filtered. The solvent is distilled off and a residue of 56.1 g of raw product is obtained.

The residue is dissolved in ether and a saturated solution of hydrogen chloride in ether is added. The precipitated crystals are filtered off and are recrystallized from acetone/isopropanol. 36.7 g of 1-methyl-2-azidomethyl-5-phenyl-1H-2,3-dihydro-1,4-benzodiazepine hydrochloride having a melting point of 181°-183° C. are obtained.

Analogously, $R_1$-2-azidomethyl-5-phenyl-1H-2,3-dihydro-1,4-benzodiazepine derivatives of Formula X can be prepared wherein A and B are substituted and $R_1$ is defined as follows:

| A | B | $R_1$ | Melting Point °C. hydrochloride |
|---|---|---|---|
| 7-$CH_3$ | H | $CH_3$ | 175-177 |
| 7-F | 3,4,5-$OCH_3$ | $CH_3$ | 123-126 base |
| 7-$CH_3$ | 3,4,5-$OCH_3$ | $CH_3$ | 187-188 |
| 8-$OCH_3$ | H | $CH_3$ | 193-194 |
| 7-$OCH_3$ | H | $CH_3$ | 203-205 |
| H | H | $CH_3$ | 187-190 |
| 7-Cl | 2-Cl | $CH_3$ | 170-173 |
| 7-F | H | $CH_3$ | 145-149 . 0.25 $H_2O$ |
| 7-Cl | H | $CH_3$ | 147-151.5 |
| H | 2-F | $C_2H_5$ | Oil* |
| 7-Br | H | $CH_3$ | Oil* |
| H | 2-Br | $CH_3$ | Oil* |
| 7-$NO_2$ | H | $CH_3$ | Oil* |
| 8-F | H | H | Oil* |

*IR-Spectra: 2120 cm$^{-1}$ (Azid/base)
Perkin-Elmer IR-Spectrophotometer 157 G

EXAMPLE 12

Tablets of the following composition per tablet are prepared:

| | |
|---|---|
| 1-methyl-2-[(thiophene-2-carbonyl)-aminomethyl]-5-phenyl-1H-2,3-dihydro-1,4-benzodiazepine | 25 mg |
| Corn Starch | 60 mg |
| Lactose | 130 mg |
| Gelatin (10% solution) | 6 mg |

The active ingredient, corn starch and lactose are worked into a paste with a 10% gelatin solution. The paste is comminuted, the resulting granulate is placed onto a suitable plate and is dried at 45° C.

The dried granulate is passed through a crushing apparatus and then is mixed in a mixer with the following components:

| | |
|---|---|
| Talcum | 5 mg |
| Magnesium stearate | 5 mg |
| Corn Starch | 9 mg |

The mixture is then pressed into tablets of 240 mg each.

EXAMPLE 13

Suppositories are prepared from the following components:

| 1-methyl-2-[(thiophene-2-carbonyl)-aminomethyl]- 5-phenyl-1H-2,3-dihydro-1,4-benzodiazepine | 25 mg |
|---|---|
| Cocoa Butter | 1975 mg |

The active ingredient and the finely triturated suppository base material are thoroughly mixed and then are melted. From the melt which is maintained homogeneous by means of stirring suppositories of 2 g each are molded.

EXAMPLE 14

A solution for parenteral injection is prepared from the following components:

| 1-methyl-2-[(thiophene-2-carbonyl)-aminomethyl]- 5-phenyl-1H-2,3-dihydro-1,4-benzodiazepine | 10% |
|---|---|
| Dimethylacetamide | 10% |
| Propylene Glycol | 50% |
| Benzyl alcohol | 1.5% |
| Ethanol | 10% |
| Water for injection purposes up to | 1 ml |

The active ingredient is dissolved in dimethylacetamide and benzyl alcohol, propylene glycol, ethanol and water are added. The solution is filtered through a filter candle and is filled into suitable ampules which then are closed and sterilized.

What is claimed is:

1. A compound selected from the group consisting of 2-acylaminomethyl-1H-2,3-dihydro-1,4-benzodiazepine derivatives of the Formula I

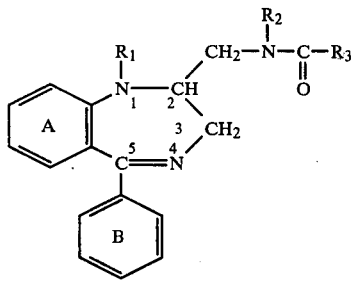

wherein
$R_1$ represents hydrogen, lower alkyl, lower alkenyl or cyclopropylmethyl,
$R_2$ represents hydrogen, lower alkyl or lower alkenyl,
$R_3$ represents a group of the formula a, b, c, or d

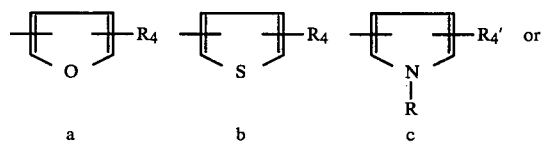

wherein R is hydrogen or $C_1$–$C_3$-alkyl, $R_4$ is hydrogen, lower alkyl, lower alkoxy, nitro or halogen, and $R_4'$ is hydrogen or $C_1$–$C_4$-alkyl, and the phenylene group A and the phenyl group B independently from each other each may be unsubstituted or be substituted by 1 to 3 substituents selected from the group consisting of halogen, lower alkylthio, lower alkoxy, lower alkyl, hydroxy, nitro and trifluoromethyl, or be substituted at two adjacent carbon atoms by methylenedioxy or ethylenedioxy, and optical isomers and pharmaceutically-acceptable acid addition salts thereof.

2. The compound as defined in claim 1 wherein $R_1$ is methyl, $R_2$ is hydrogen, $R_3$ is a group of Formula b.

3. The compound as defined in claim 2 wherein $R_3$ is 2-thiophene.

4. The compound as defined in claim 3 wherein B is unsubstituted phenyl and A is unsubstituted phenylene or phenylene substituted by 7-fluoro, 7-methyl, 7-isopropyl, 6, 8-dimethyl, 7,8-dimethyl, 7-methoxy, 7-n-propyloxy, 7,8-methylenedioxy, 7,8-ethylenedioxy, 7-trifluoromethyl, 7-nitro, 7,8-dimethoxy, 6,8-dimethoxy, 8-fluoro, 8-chloro, 8-ethyl, 8-methylthio, 8-methoxy or 8-ethyloxy.

5. The compound as defined in claim 3 wherein A is unsubstituted phenylene and B is unsubstituted phenyl, 2-fluorophenyl, 3-methoxyphenyl, 2,6-dimethoxyphenyl or 3,4-dimethoxyphenyl.

6. The compound as defined in claim 3 wherein A is phenylene substituted by 7-fluoro, 7-bromo, 7-methyl, 8-methoxy or 7, 8-methylenedioxy and B is 2-fluorophenyl, 3-fluorophenyl, 4-fluorophenyl, 2-chlorophenyl, 2-bromophenyl, 2-methylphenyl, 2-trifluoromethylphenyl, 3-trifluoromethylphenyl, 4-trifluoromethylphenyl or 3,4,5-trimethoxyphenyl.

7. The compound as defined in claim 2 wherein A is unsubstituted phenylene or phenylene substituted by 7-fluoro, 8-fluoro, 7-methyl, 8-methylthio, 7-methoxy, 8-methoxy, 8-ethyloxy, 7-n-propyloxy or 7,8-methylenedioxy, and B is unsubstituted phenyl, 2-fluorophenyl, 3-fluorophenyl, 4-fluorophenyl or 3,4,5-trimethoxyphenyl, and $R_3$ is a group of the formula

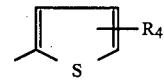

wherein $R_4$ is 5-chloro, 4-bromo, 5-bromo, 3-methyl, 4-methyl, 5-methyl, 5-ethyl, 5-methoxy or 5-ethyloxy.

8. The compound as defined in claim 2 wherein $R_3$ is 3-thiophene, B is unsubstituted phenyl and A is phenylene substituted by 7-methyl, 8-methyl, 9-methyl, 8-ethyl, 7-n-propoxy, 7-isopropyl, 7-methoxy, 8-methoxy, 8-ethoxy, 8-methylthio, 6,8-dimethyl or 7,8-dimethyl.

9. The compound as defined in claim 2 wherein $R_3$ is a group of the formula

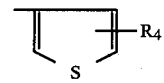

wherein $R_4$ is hydrogen or 2-methyl, A is unsubstituted phenylene or phenylene substituted by 7-fluoro, 7-bromo, 7-chloro-8-methoxy, 7-fluoro-8-methoxy, 7-methyl, 8-methyl, 9-methyl, 6-methoxy, 8-methoxy, 8-ethyloxy, 8-isopropyloxy, 8-nitro, 8-methyl-6-methoxy, 7,8-methylenedioxy, 6,7-methylenedioxy, 6-hydroxy, 7,8-dimethoxy and B is phenyl, 2-fluorophenyl, 2-chlorophenyl, 3-methoxyphenyl, 4-methoxyphenyl, 3,4-dimethoxyphenyl, 3,4,5-trimethoxyphenyl, 3-trifluoromethylphenyl or 4-trifluoromethylphenyl.

10. The compound as defined in claim 1 wherein $R_1$ is methyl, $R_2$ is hydrogen and $R_3$ is a group of formula a and A and B are as defined in claim 1.

11. The compound as defined in claim 10 wherein $R_3$ is a group of the formula

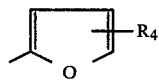

wherein $R_4$ is hydrogen, 5-methyl or 5-nitro, A is unsubstituted phenylene or phenylene substituted by 7-fluoro, 7-bromo, 7-methyl, 8-ethyl, 7-isopropyl, 8-methylthio, 6,8-dimethyl, 7,8-dimethyl, 7-methoxy, 6,8-dimethoxy, 7,8-dimethoxy, 7-n-propyloxy, 8-methoxy, 7,8-methylenedioxy or 7-chloro, and B is phenyl, 2-chlorophenyl, 2-fluorophenyl, 3-methoxyphenyl, 3,4-dimethoxyphenyl, or 3,4,5-trimethoxyphenyl.

12. The compound as defined in claim 10 wherein $R_3$ is a group of the formula

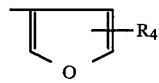

wherein $R_4$ is hydrogen, 2-methyl or 5-methyl, A is unsubstituted phenylene or phenylene substituted by 7-chloro, 8-chloro, 7-fluoro, 8-fluoro, 7-fluoro-8-methoxy, 8-nitro, 7-methyl-9-chloro, 8-methylthio, 7-methyl, 8-methyl, 8-methyl-6-methoxy, 8-ethyl, 7-isopropyl, 7,8-dimethyl, 6,8-dimethyl, 7-methoxy, 8-methoxy, 8-ethyloxy, 7-n-propyloxy, 8-isopropyloxy, 7,8-dimethoxy, 7,8-methylenedioxy, or 7,8-ethylenedioxy, and B is phenyl, 2-fluorophenyl, 3-fluorophenyl, 4-fluorophenyl, 2-bromophenyl, 2-chlorophenyl, 2-methylphenyl, 2-trifluoromethylphenyl, 3-trifluoromethylphenyl, 4-trifluoromethylphenyl, 2,6-difluorophenyl, 3-trifluoromethyl-4-chlorophenyl, 2,4-dichlorophenyl, 2-methoxyphenyl, 3-methoxyphenyl, 4-methoxyphenyl, 2,6-dimethoxyphenyl, 3,4-dimethoxyphenyl, 2,3-dichlorophenyl, 3,4,5-trimethoxyphenyl or 2,4-difluorophenyl.

13. The compound as defined in claim 1 wherein $R_1$ is methyl, $R_2$ is hydrogen, $R_3$ is 1H-pyrrol, 1-methylpyrrol or 1,2-dimethylpyrrol, A is unsubstituted phenylene or phenylene substituted by 8-methyl, 8-methoxy or 7,8-methylenedioxy, and B is phenyl, 2-fluorophenyl, 2-bromophenyl, 2-methylphenyl or 2-methoxyphenyl.

14. The compound as defined in claim 1 wherein $R_1$ is methyl, $R_2$ is hydrogen, $R_3CO$ is picolinoyl, nicotinoyl or isonicotinoyl, A is unsubstituted phenylene or phenylene substituted by 7-bromo, 7-chloro or 8-methoxy and B is phenyl, 2-fluorophenyl or 2-chlorophenyl.

15. The compound as defined in claim 1 wherein $R_2$ is hydrogen, methyl, ethyl, n-propyl or allyl.

16. The compound as defined in claim 1 wherein $R_1$ is hydrogen, methyl, ethyl, n-propyl, i-propyl, n-butyl or cyclopropylmethyl.

17. 1-methyl-2-[(thiophene-3-carbonyl)-aminomethyl]-5-(2-fluorophenyl)-1H-2,3-dihydro-1,4-benzodiazepine.

18. A pharmaceutical composition comprising an analgesically effective amount of at least one compound as defined in claim 1 and a pharmaceutically acceptable carrier.

19. A pharmaceutical composition comprising an analgesically effective amount of the compound as defined in claim 17 and a pharmaceutically acceptable carrier.

20. A method of treating pain disorders in larger mammals which comprises administering to a larger mammal an effective amount of a compound as defined in claim 1.

21. A method of treating pain disorders in larger mammals which comprises administering to a larger mammal an effective amount of a compound as defined in claim 17.

* * * * *